United States Patent [19]

Merkle et al.

[11] Patent Number: 5,569,769
[45] Date of Patent: Oct. 29, 1996

[54] PREPARATION OF PYRAZOLE AND ITS DERIVATIVES

[75] Inventors: Hans R. Merkle, Ludwigshafen; Erich Fretschner, Neckarsteinach, both of Germany

[73] Assignee: BASF Aktiengesellschaft, Ludwigshafen, Germany

[21] Appl. No.: 596,376

[22] PCT Filed: Aug. 13, 1994

[86] PCT No.: PCT/EP94/02708

§ 371 Date: Feb. 15, 1996

§ 102(e) Date: Feb. 15, 1996

[87] PCT Pub. No.: WO95/06036

PCT Pub. Date: Mar. 2, 1995

[30] Foreign Application Priority Data

Aug. 23, 1993 [DE] Germany .................. 43 28 228.8

[51] Int. Cl.⁶ .................................. C07D 231/12
[52] U.S. Cl. .................................. 548/373.1
[58] Field of Search .......................... 548/373.1

[56] References Cited

U.S. PATENT DOCUMENTS 4,996,327  2/1991  Merkle et al. .
5,128,480  7/1992  Merkle et al. .

FOREIGN PATENT DOCUMENTS 1141390  2/1983  Canada .
  20964  1/1981  European Pat. Off. .
 366327  5/1990  European Pat. Off. .
 402722  12/1990  European Pat. Off. .
 474037  3/1992  European Pat. Off. .

OTHER PUBLICATIONS

Advances in Heterocyclic Chemistry, Katritzky, vol. 6, 1966.
Pyrazoles, Pyrazolines, Pyrazolidines, Idazoles and Condensed Rings, Behr et al., The Chemistry of Heterocyuclic Compounds, 1967.

Primary Examiner—Robert W. Hamsuer
Attorney, Agent, or Firm—Keil & Weinkauf

[57] ABSTRACT

A process for preparing pyrazole and its derivatives of the formula I

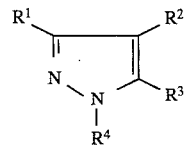

where $R^1$, $R^2$, $R^3$ and $R^4$ are each hydrogen, halogen, nitro, carboxyl, sulfonyl or C-organic radicals, from alpha,beta-unsaturated carbonyl compounds of the formula II

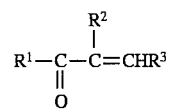

and hydrazine or hydrazine derivatives of the formula III

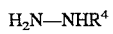

wherein, initially without additional diluent, an alpha,beta-unsaturated carbonyl compound of the formula II is reacted with hydrazine or a hydrazine derivative of the formula III, and the resulting reaction mixture is reacted in another step with a mixture of sulfuric acid and iodine or a compound which liberates iodine or hydrogen iodide.

6 Claims, No Drawings

PREPARATION OF PYRAZOLE AND ITS DERIVATIVES

The present invention relates to a process for preparing pyrazole and its derivatives of the formula I

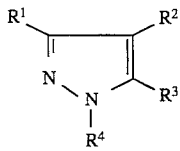

where $R^1$, $R^2$, $R^3$ and $R^4$ are each hydrogen, halogen, nitro, carboxyl, sulfonyl or C-organic radicals, from alpha,beta-unsaturated carbonyl compounds of the formula II

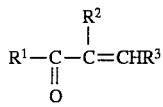

and hydrazine or hydrazine derivatives of the formula III

EP-A 402 722 discloses the preparation of pyrazole and its derivatives from alpha,beta-unsaturated carbonyl compounds and hydrazine or hydrazine derivatives. In the process described therein, either pyrazoline or a carbonyl compound and a hydrazine derivative is reacted in a mixture of sulfuric acid and iodine or a compound which liberates iodine or hydrogen iodide in situ to give the required pyrazole. The yields in the described examples average 78% based on the hydrazine derivative employed.

It is an object of the present invention to prepare pyrazole and its derivatives in a simple manner with improved yields and in higher purity.

We have found that this object is achieved by a process for preparing pyrazole and its derivatives of the formula I

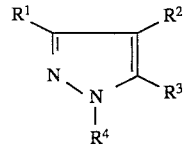

where $R^1$, $R^2$, $R^3$ and $R^4$ are each hydrogen, halogen, nitro, carboxyl, sulfonyl or C-organic radicals, from alpha,beta-unsaturated carbonyl compounds of the formula II

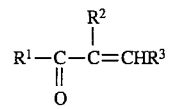

and hydrazine or hydrazine derivatives of the formula III

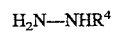

wherein, initially without additional diluent, an alpha,beta-unsaturated carbonyl compound of the formula II is reacted with hydrazine or a hydrazine derivative of the formula III, and the resulting reaction mixture is reacted in another step with a mixture of sulfuric acid and iodine or a compound which liberates iodine or hydrogen iodide.

In this process, initially an alpha,beta-unsaturated carbonyl compound II is mixed with hydrazine or a hydrazine derivative III while maintaining the temperature in the reaction medium during the admixture from to 100° C., preferably 10° C. to 70° C., in particular 20° C. to 50° C. Since the reaction of alpha,beta-unsaturated carbonyl compounds II with hydrazine or a hydrazine derivative III is exothermic, it may be necessary to cool the reaction mixture during the admixture. For the mixing it is immaterial which of the reactants is introduced first or whether the starting materials are introduced into the reaction volume simultaneously but separately. Mixing is completed normally by stirring at the mixing temperature for from 10 minutes to 60 minutes after the addition is complete.

Findings to date indicate that longer stirring times have a negligible effect on the completion of the reaction.

The starting materials are generally reacted together in approximately the stoichiometric amounts, the ratio of carbonyl compound II to hydrazine derivative III normally being from 1:0.65 to 1:1.25 mol/mol. A different ratio of the reactants has a negligible effect on the progress of the reaction and is not worthwhile for economic reasons.

Hydrazine or the hydrazine derivative III can be used either in the form of the hydrates or of the free bases or also in the form of corresponding hydrazonium salts for the present process. Use of salts which are insoluble in the reaction medium may lead to losses of yield owing to inadequate mixing. The hydrates or the free bases of the hydrazine derivatives III are preferably used.

The process is based on the principle of initially forming, by reaction of hydrazines with α,β-unsaturated carbonyl compounds, the corresponding pyrazolines and secondary products. Workup by distillation after removal of the water of reaction provides only moderate yields because the pyrazolines are accompanied by the byproducts which are formed by addition of the pyrazolines onto the initial carbonyl compounds and which in turn may form hydrazones and azines with the hyrazines.

The resulting reaction mixture is subsequently, without further workup, reacted with a mixture of sulfuric acid and iodine or a compound which liberates iodine or hydrogen iodide. The procedure for this is normally as stated in EP-A 402 722, ie. a mixture of sulfuric acid and iodine or a compound which liberates iodine or hydrogen iodide is heated to from 50° C. to 250° C., preferably 70° C. to 200° C., in particular 100° C. to 180° C. and the reaction mixture from the first stage is added at this temperature.

It is also possible to introduce the reaction mixture from the first stage into the mixture of sulfuric acid and iodine or a compound which liberates iodine or hydrogen iodide at lower temperatures, for example 10°–30° C. However, for technical reasons, it is advantageous to carry out the addition at a higher temperature because salts are formed on mixing, and stirring of the reaction mixture becomes more difficult. Findings to date indicate that the temperature during the addition has no effect on the yield of the reaction.

This second stage probably essentially obeys the same principle as the reaction described in EP-A 402 722. According to this, sulfuric acid is generally used in a concentration of not less than 30% by weight. The sulfuric acid is normally from 40 to 99% by weight, preferably 45 to 95% by weight.

The amount of iodine or compound which liberates iodine or hydrogen iodide in this reaction is generally from 0.01 to 10 mol %, preferably from 0.05 to 5 mol %, in particular from 0.1 to 2 mol %, based on the hydrazine or the hydrazine derivative III.

Besides iodine and hydrogen iodide, suitable compounds which liberate iodine or hydrogen iodide are, for example, alkali metal and alkaline earth metal iodides such as lithium iodide, sodium iodide, potassium iodide, cesium iodide, magnesium iodide and calcium iodide as well as other metal iodides; it is possible in principle to employ all compounds of iodine or hydrogen iodide which are able to liberate iodine or hydrogen iodide under the reaction conditions. These include, for example, other organic iodine compounds such as alkali metal, alkaline earth metal or other metal hypoiodites, iodites, iodates and periodates or organic iodine compounds, for example alkyl iodides such as methyl iodide.

It has emerged that the optimal temperature for the dehydrogenation reaction or the oxidation of the iodide to iodine depends on the sulfuric acid concentration. The necessary temperatures for the reaction increase as the sulfuric acid concentration decreases. It is therefore advisable to remove the water of reaction and the water introduced by the use of hydrates by distillation during the reaction in order to keep the temperature low.

The water removed from the reaction contains a large part of the added iodide as iodine and hydrogen iodide, which can be recovered after reduction or neutralization with, for example, sodium bisulfite.

After the reaction is complete, the reaction mixture is allowed to cool, whereupon the pyrazole derivative generally crystallizes as sulfate.

To liberate the pyrazole, the reaction mixture is neutralized and the neutral mixture is extracted with an inert organic water-immiscible solvent. The organic phase is subsequently dried and worked up in a conventional way. This results in crude pyrazoles which have a purity of 85–90% which can be increased to 99% by a single distillation.

The abovementioned process is suitable for preparing pyrazole and its derivatives of the general formula I

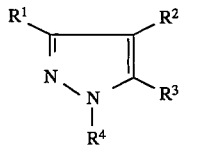

where $R^1$, $R^2$, $R^3$ and $R^4$ are each, independently of one another, hydrogen, halogen, nitro, carboxyl, sulfonyl or C-organic radicals.

Halogen means in this connection in particular fluorine, chlorine and bromine.

Suitable C-organic radicals are:

alkyl groups which can be straight-chain or branched, for example $C_1$–$C_{10}$-alkyl, preferably $C_1$–$C_8$-alkyl, especially $C_1$–$C_6$-alkyl, it being possible for these radicals in turn to be interrupted by hetero atoms such as nitrogen, oxygen and sulfur and to carry substituents from the following group: nitro, carboxyl, sulfonyl, halogen, cycloalkyl, bicycloalkyl, aryl and hetaryl;

cycloalkyl groups or bicycloalkyl groups, for example $C_3$–$C_8$-cycloalkyl or $C_6$–$C_{10}$-bicycloalkyl, it being possible for these radicals in turn to be interrupted by hetero atoms such as nitrogen, oxygen and sulfur and to carry substituents from the following group: nitro, carboxyl, sulfonyl, halogen, alkyl, cycloalkyl, bicycloalkyl, aryl and hetaryl;

aryl groups or hetaryl groups such as phenyl, naphthyl and pyridyl, it being possible for these radicals in turn to carry substituents from the following group: nitro, carboxyl, sulfonyl, halogen, alkyl, cycloalkyl, bicycloalkyl, aryl and hetaryl.

The present process is particularly suitable for preparing pyrazole derivatives in which at least one of the radicals $R^1$ to $R^4$ is not hydrogen.

Pyrazole and its derivatives are used, for example, as intermediates for preparing pharmacologically active compounds, crop protection agents or else dyes.

EXAMPLES

1. Preparation of 3-methylpyrazole 1.a Reaction of crotonaldehyde and hydrazine hydrate 169.1 g (2.415 mol) of crotonaldehyde were added to 115 g (2.3 mol) of hydrazine hydrate keeping the temperature at 30° C. by cooling. After the addition was complete, the mixture was stirred at 25° C. to 30° C. for a further 30 min.

1.b Conversion into 3-methylpyrazole

A mixture of 720.8 g (5.06 mol) of 68.8% strength sulfuric acid and 0.76 g (5.1 mmol) of sodium iodide was heated to 155° C. and, at this temperature, the mixture obtained in 1.a was added. Water was distilled out during the addition and for a further 30 min after the addition was complete. The water removed in this way was added to the reaction mixture, after it had been cooled to 70° C., to dilute it.

The diluted reaction mixture was adjusted to pH 8.5–9 with 15% strength sodium hydroxide solution. A large part of the product resulted as an oil from this neutralization and can be removed by decantation. Extraction of the aqueous phase with isobutanol and subsequent workup of the collected organic phases by distillation resulted in 172.5 g of 3-methylpyrazole (90.55% based on hydrazine hydrate) of 99% purity (HPLC determination). Boiling point 88° C./10 mbar.

2. Preparation of 4-methylpyrazole 2.a Reaction of methacrolein and hydrazine hydrate 177.1 g (2.53 mol) of methacrolein were added to 115 g (2.3 mol) of hydrazine hydrate keeping the temperature at 30° C. by cooling. After the addition was complete, the mixture was stirred at 25° C. to 30° C. for a further 30 min.

2.b Conversion into 4-methylpyrazole

A mixture of 720.8 g (5.06 mol) of 68.8% strength sulfuric acid and 1.00 g (6.7 mmol) of sodium iodide was heated to 155° C. and, at this temperature, the mixture obtained in 2.a was added. Water was distilled out during the addition and for a further 30 min after the addition was complete. The water removed in this way was added to the reaction mixture, after it had been cooled to 50° C., to dilute it.

The diluted reaction mixture was adjusted to pH 8.5 with 15% strength sodium hydroxide solution. A large part of the product resulted as an oil from this neutralization and can be removed by decantation. Extraction of the aqueous phase with isobutanol and subsequent workup of the collected organic phases by distillation resulted in 170.5 g of 4-methylpyrazole (89.52% based on hydrazine hydrate) of 99.2% purity (HPLC determination). Boiling point 82° C./7 mbar.

3. Preparation of 3,4-dimethylpyrazole 3.a Reaction of trans-2,3-dimethylacrolein with hydrazine hydrate 22.1 g (0.2625 mol) of trans-2,3-dimethylacrolein were added to 15.6 g (0.25 mol) of 80% hydrazine hydrate keeping the temperature at 30° C. by cooling. After the addition was complete, the mixture was stirred at 25° C. to 30° C. for a further 30 min.

3.b Conversion into 3,4-dimethylpyrazole

A mixture of 74.2 g (0.52 mol) of 68.8% strength sulfuric acid and 0.5 g (3.3 mmol) of sodium iodide was heated to 155° C. and, at this temperature, the mixture obtained in 3.a was added. Water was distilled out during the addition and for a further 30 min after the addition was complete. The water removed in this way was added to the reaction mixture, after it had been cooled to 50° C., to dilute it.

The diluted reaction mixture was adjusted to pH 8.5 with 15% strength sodium hydroxide solution. A large part of the product resulted as an oil from this neutralization and can be removed by decantation. Extraction of the aqueous phase with isobutanol and subsequent workup of the collected organic phases by distillation resulted in 21.4 g of 3,4-dimethylpyrazole (88.4% based on hydrazine hydrate) of 99.2% purity. Boiling point 96° C./10 mbar.

4. Preparation of 1,5-dimethylpyrazole 4.a Reaction of crotonaldehyde with methylhydrazine 147 g (2.1 mol) of crotonaldehyde were added to 92 g (2 mol) of methylhydrazine keeping the temperature at 30° C. by cooling. After the addition was complete, the mixture was stirred at 25° C. to 30° C. for a further 30 min.

4.b Conversion into 1,5-dimethylpyrazole

A mixture of 626.7 g (4.4 mol) of 68.8% strength sulfuric acid and 0.66 g (4.4 mmol) of sodium iodide was heated to 155° C. and, at this temperature, the mixture obtained in 4.a was added. Water was distilled out during the addition and for a further 30 min after the addition was complete. The water removed in this way was added to the reaction mixture, after it had been cooled to 70° C., to dilute it.

The diluted reaction mixture was adjusted to pH 8.5–9 with 15% strength sodium hydroxide solution. A large part of the product resulted as an oil from this neutralization and can be removed by decantation. Extraction of the aqueous phase with isobutanol and subsequent workup of the collected organic phases by distillation resulted in 167.8 g of 1,5-dimethylpyrazole (86.7% based on methylhydrazine hydrate) of 99.2% purity. Boiling point 157° C./1013 mbar.

5. Preparation of 3-methylpyrazole 5.a Reaction of crotonaldehyde with hydrazine hydrate 147 g (2.1 mol) of crotonaldehyde were added to 125 g (2.0 mol) of 80% hydrazine hydrate keeping the temperature at 30° C. by cooling. After the addition was complete, the mixture was stirred at 25° C. to 30° C. for a further 30 min.

5.b Conversion into 3-methylpyrazole

The mixture obtained in 5.a was added at 25° C. to a mixture of 449.2 g (4.4 mol) of 95% strength sulfuric acid and 0.66 g (4.4 mmol) of sodium iodide keeping the temperature at 25° C. by cooling. The reaction mixture was then heated to 125° C. over the course of 45 min and kept at 125° C. for 60 min. Water was distilled out during the heating up and during the subsequent stirring. The water removed in this way was added to the reaction mixture, after it had been cooled to 70° C., to dilute it.

The diluted reaction mixture was adjusted to pH 8.5–9 with 10% strength sodium hydroxide solution. A large part of the product resulted as an oil from this neutralization and can be removed by decantation. Extraction of the aqueous phase with isobutanol and subsequent workup of the collected organic phases by distillation resulted in 143.4 g of 3-methylpyrazole (87% based on hydrazine hydrate) of 99.5% purity. Boiling point 88° C./10 mbar. Comparison of the process according to the invention with the process disclosed in EP-A-402 722

A. Preparation of 3-methylpyrazole by the process according to the invention

A.1 Reaction of crotonaldehyde and hydrazine hydrate 73.5 g (1.05 mol) of crotonaldehyde were added to 62.5 g (1.0 mol) of 80% hydrazine hydrate keeping the temperature at 30° C. by cooling. After the addition was complete, the mixture was stirred at 25° C. to 30° C. for a further 30 min.

A.2 Conversion into 3-methylpyrazole

A mixture of 313.6 g (2.2 mol) of 68.8% strength sulfuric acid and 0.33 g (2.2 mmol) of sodium iodide was heated to 155° C. and, at this temperature, the mixture obtained in A.1 was added. Water was distilled out during the addition and for a further 30 min after the addition was complete. The water removed in this way was added to the reaction mixture after cooling.

The diluted reaction mixture was adjusted to pH 8.5 with 15% strength sodium hydroxide solution. A large part of the product resulted as an oil from this neutralization and can be removed by decantation. Extraction of the aqueous phase with isobutanol and subsequent workup of the collected organic phases by distillation resulted in 73.4 g of 3-methylpyrazole (89% based on hydrazine hydrate) of 99.5% purity (HPLC determination). Boiling point 88° C./10 mbar.

B Preparation of 3-methylpyrazole by the process disclosed in EP-A 402 722

B.1 A mixture of 313.6 g (2.2 mol) of 68.8% strength sulfuric acid and 0.33 g (2.2 mmol) of sodium iodide was heated to 155° C. and, at this temperature, 62.5 g (1 mol) of 80% hydrazine hydrate and 73.6 g (1.05 mol) of crotonaldehyde were added simultaneously. Water was distilled out during the addition and for a further 30 min after the addition was complete. The water removed in this way was added to the reaction mixture, after it had been cooled to 50° C., to dilute it.

B.2 The diluted reaction mixture was adjusted to pH 8.5 with 15% strength sodium hydroxide solution. A large part of the product resulted as an oil from this neutralization and was removable by decantation. Extraction of the aqueous phase with isobutanol and subsequent workup of the collected organic phases by distillation resulted in 62.4 g of 3-methylpyrazole (75.7% based on hyrazine hydrate) of 99.5% purity. Boiling point: 88° C./10 mbar).

We claim:

1. A process for preparing pyrazole and its derivatives of the formula I

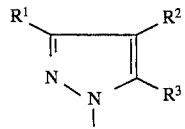

where $R^1$, $R^2$, $R^3$ and $R^4$ are each hydrogen, halogen, nitro, carboxyl, sulfonyl or C-organic radicals, from alpha,beta-unsaturated carbonyl compounds of the formula II

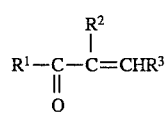

and hydrazine or hydrazine derivatives of the formula III

wherein, initially without additional diluent, an alpha,beta-unsaturated carbonyl compound of the formula II is reacted with hydrazine or a hydrazine derivative of the formula III, and the resulting reaction mixture is reacted in another step with a mixture of sulfuric acid and iodine or a compound which liberates iodine or hydrogen iodide.

2. A process as claimed in claim 1, wherein the reaction of the alpha,beta-unsaturated carbonyl compound of the formula II with hydrazine or a hydrazine derivative of the formula III is carried out at from 0° C. to 100° C.

3. A process as claimed in claim 1, wherein from 40 to 99% by weight of sulfuric acid is used.

4. A process as claimed in claim 1, wherein from 0.01 to 10 mol % of iodine or of a compound which liberates iodine or hydrogen iodide, based on the hydrazine or the hydrazine derivative of the formula III, are used.

5. A process as claimed in claim 1, wherein the reaction mixture obtained from the reaction of alpha,beta-unsaturated carbonyl compound of the formula II with hydrazine or a hydrazine derivative of the formula III is reacted at from 50° C. to 250° C. with a mixture of sulfuric acid and iodine or a compound which liberates iodine or hydrogen iodide.

6. A process as claimed in claim 1, wherein, during the reaction of the reaction mixture obtained from the reaction of the alpha,beta-unsaturated carbonyl compound of the formula II with hydrazine or a hydrazine derivative of the formula III with a mixture of sulfuric acid and iodine or a compound which liberates iodine or hydrogen iodide, the water of reaction present in the mixture is removed.

* * * * *